Figure 1A:
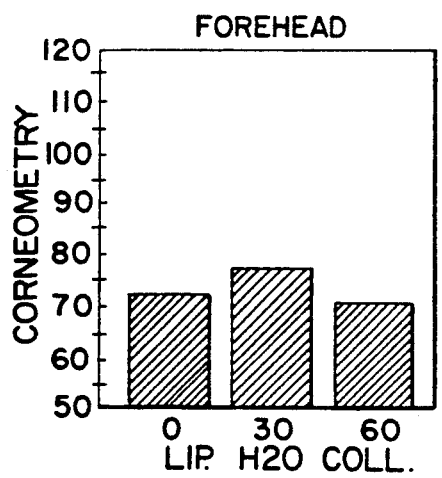
Figure 1B:
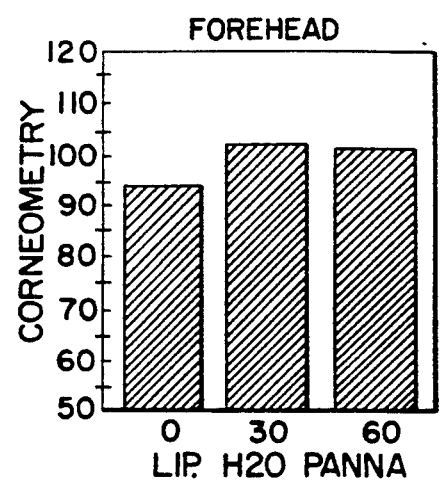
Figure 2A:
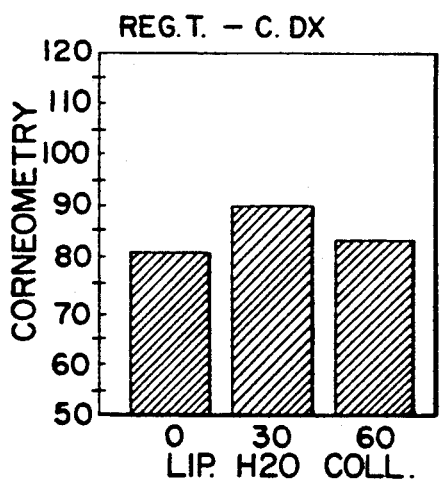
Figure 2B:
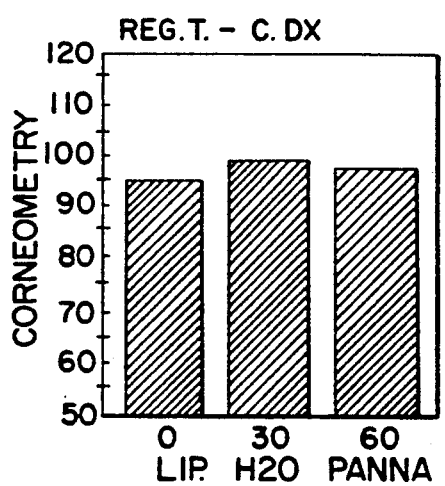
Figure 3A:
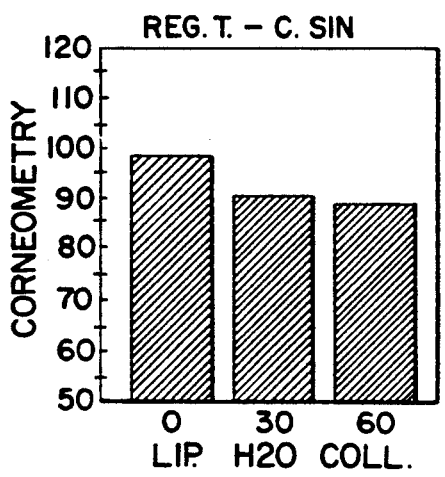
Figure 3B:
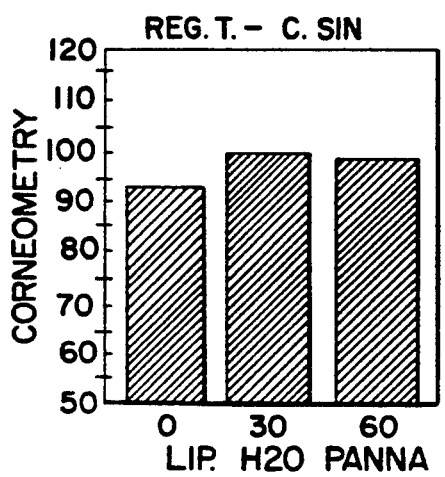
Figure 4A:
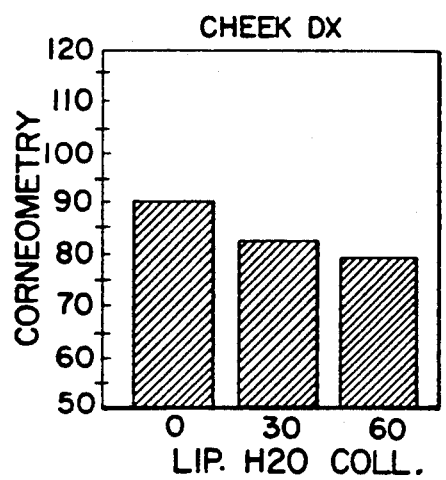
Figure 4B:
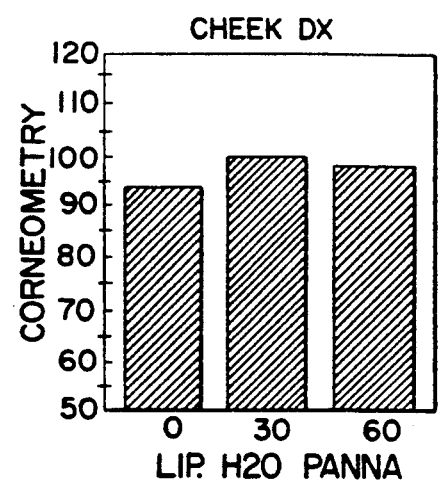
Figure 5A:
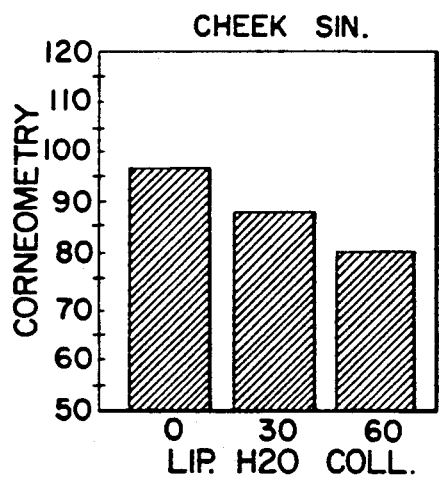
Figure 5B:
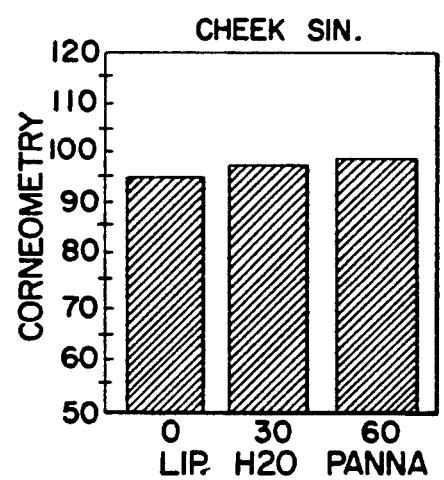
Figure 6A:
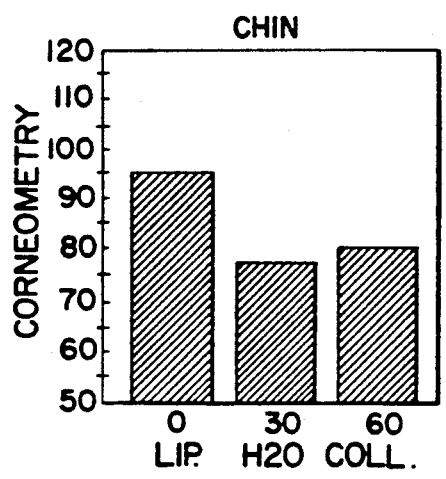
Figure 6B:
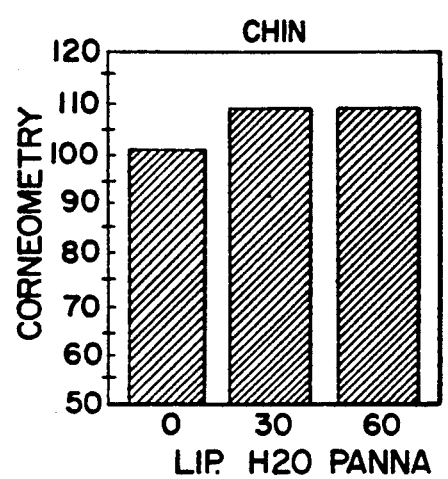

United States Patent [19]

Bertini

[11] Patent Number: 5,106,624
[45] Date of Patent: Apr. 21, 1992

[54] METHOD FOR AN EFFECTIVE MOISTURIZING TREATMENT OF THE SKIN, PARTICULARLY USEFUL IN COSMETICS APPLICATIONS

[75] Inventor: Sergio C. Bertini, Milan, Italy

[73] Assignee: Cosmetici Sorgente Panna S.p.A., Milan, Italy

[21] Appl. No.: 681,450

[22] Filed: Apr. 4, 1991

Related U.S. Application Data

[63] Continuation of Ser. No. 134,767, Dec. 18, 1987, abandoned.

[30] Foreign Application Priority Data

Dec. 19, 1986 [IT] Italy ................... 22795 A/86

[51] Int. Cl.$^5$ .................. A61K 9/27; A61K 7/48; B01J 13/02
[52] U.S. Cl. ................ 424/401; 428/402.2; 264/4.1; 514/847; 424/450
[58] Field of Search ............ 428/402.2; 424/450, 424/401; 514/847

[56] References Cited

U.S. PATENT DOCUMENTS

| | | | |
|---|---|---|---|
| 3,957,971 | 5/1976 | Oleniacz | 424/70 |
| 4,247,411 | 1/1981 | Vanlerberghe et al. | 428/402.2 X |
| 4,670,185 | 6/1987 | Fujiwara et al. | 264/4.1 X |
| 4,767,463 | 8/1988 | Brode et al. | 424/70 X |
| 4,772,471 | 9/1988 | Vanlerberghe et al. | 424/450 |
| 4,792,571 | 12/1988 | Schiltz et al. | 514/2 X |

FOREIGN PATENT DOCUMENTS

| | | |
|---|---|---|
| 300199 | 7/1972 | Austria . |
| 0180559 | 5/1986 | European Pat. Off. . |
| 2473887 | 7/1981 | France . |
| 2540381 | 8/1984 | France . |
| 2013609 | 8/1979 | United Kingdom . |

OTHER PUBLICATIONS

Varma et al., "Mucopolysaccharides-Glycosaminoglycans of Body Fluids in Health & Disease", W. de Gruiter, ed., Berlin—New York, pp. 22-27 (1983).
Horowitz et al., eds. "The Glycoconjugates", vol. II, Academic Press, Inc., New York, pp. 10-14 (1978).
Curri, S. B., *Biochemistry and Exptl. Biology*, vol. 13, No. 3, pp. 245-261.

*Primary Examiner*—Robert L. Stoll
*Assistant Examiner*—John M. Covert
*Attorney, Agent, or Firm*—Birch, Stewart, Kolasch & Birch

[57] ABSTRACT

A method and product for moisturizing the human skin which comprises topically applying to the skin a composition comprising liposomes and mineral water.

13 Claims, 3 Drawing Sheets

METHOD FOR AN EFFECTIVE MOISTURIZING TREATMENT OF THE SKIN, PARTICULARLY USEFUL IN COSMETICS APPLICATIONS

This application is a continuation of application Ser. No. 07/134,767 filed on December 18, 1987, now abandoned.

DESCRIPTION

This invention relates to a method of carrying out an effective skin moisturizing treatment particularly, though not exclusively, for use in cosmetics.

It is known that a substantial proportion of the cosmetics research work has had for its primary object the provision of providing substances, preparations, formulations, and methods for moisturizing the skin in an effective and successful way.

Also known is the fact that research work in cosmetics has long focused on liposomes (acqueous microdispersions of phospholipids) on account of their lamellar (uni- or multi-lamellar) structure resembling the cell membrane and, hence, being capable of breaking through the skin barrier, and on their ability to trap water and then carry it through the various layers of skin to be moisturized.

The use of liposomes as water carriers or even as carriers of substances, active principles, and the like, in a trapped or dissolved state through the interlammellar water or core water of liposomes, has been extensively proposed and even substantiated experimentally.

However, at the level of skin moisturizing as such, the effectiveness of the methods investigated and tested heretofore has failed to prove entirely satisfactory. For example, the well-recognized softing action of a liposome-based treatment is invariably of very short duration, possibly because it is due to the mere contribution of exogenous water to those cells which lie closest to the surface, and apt therefore to evaporate quickly.

In order to achieve deeper penetration through the skin layers and an increased moisturizing effect, it has long been suggested and even proved, that humectant additives be employed such as glycerol, urea, sorbitol, pyroglutamate, etc.

However, while on the one hand, the moisturizing effect aimed at may be said to have been improved and to be satisfactory, on the other hand, the incorporation of said substances and/or additives to liposomes involves a whole series of operations which are not easily carried out and hinder the preparation of such liposomes on an industrial scale, in a somewhat disheartening way from both the technical and economical standpoints.

The problem underlying the present invention is to provide a method for an effective skin moisturizing treatment which can overcome the prior art drawbacks noted above, viz. a method which affords a better than satisfactory moisturizing of the skin not merely affecting the surface layers thereof and involving no special and difficult techniques for preparing and storing respective liposomes on a commercial scale.

This problem is solved according to the present invention by a method of moisturizing the skin, particularly for cosmetics applications, characterized in that mineral water is topically administered to the skin utilizing liposomes as a carrier.

According to one aspect of the present invention, the liposomes used in said administering step are prepared (by conventional techniques) in mineral water, specifically oligomineral water.

In accordance with a further feature of the present invention, mineral water is administered utilizing of liposomes, with said water being delivered in a nebulized or atomized state from small bottles wherein the liposomic mineral water and a suitable propellant have been previously packaged.

Further features and advantages of the present invention will become more clearly apparent from the following description of a non-limitative exemplary embodiment of the inventive method, with the results thereof being compared to those from the prior art.

In the drawings:

The present invention will become more fully understood from the detailed description given hereinbelow and the accompanying drawings which are given by way of illustration only, and thus, are not limitative of the present invention, and wherein:

FIGS. 1A to 7A show histograms relating to experimental data measured on patients subjected to a liposome treatment in accordance with conventional techniques, and FIGS. 1B to 7B show similar histograms relating to experimental data measured on patients subjected to a moisturizing treatment according to the present invention.

EXAMPLE 1

2 g of purified lecithin are dispersed by ultrasonic in 100 ml of oligomineral water which was commercially available by the trade name "SORGENTE PANNA".

This was followed by a treatment in accordance with Deamer et al, Biochem. Biophys. ACTA, (1976), pp. 446, 629 and 634, with the addition of 500 mg of immediate biochemical precursors of asulfurate glucosaminoglycanes (GAG). After stirring for 20 minutes, the solution is allowed to settle for 24 hours, and the substrate is then filtered to yield an opalescent microdispersion which is additivated with conventional preservatives in appropriate amounts.

The oligomineral water liposomes thus obtained are subsequently packaged in small spray bottles using nitrogen as a the preferred propellant.

The thus packaged product is then delivered to storage.

EXAMPLE 2

Using the same procedure as described for the preparation of oligomineral water liposomes, demineralized water liposomes were prepared from the same phospholipides (lecithin) but using instead of the GAG precursors, a 10% collagen solution. The stratum corneum moisturizing properties thereof are extensively described in the cosmetological literature.

The resulting demineralized water liposomes were again packaged in small spray bottles using a propellant selected from inert gases, specifically nitrogen. The bottles were then delivered to storage.

10 female patients whose age varied between 30 and 58 years were subjected to measurement of the moisturizing gradient in the stratum corneum, using the CORNEOMETER CM 420 meter according to Schrader. The measurements were carried out under basal conditions at 30 and 60 minutes from application of the liposomal preparation (demineralized water liposomes and collagen) as per Example 2, to the skin of the forehead, right and left temporal and cheekbone regions, right and left cheeks, and chin.

A second group of 20 female individuals, whose age varied from 18 to 42 years, were subjected to measurement of the stratum corneum values in the same regions of the face and after the same time period as in the preceding test, by carrying out the treatment with "SORGENTE PANNA" oligomineral water liposomes as obtained in Example 1.

The data were subjected to statistical analysis, computing the means±D.S. and the significance of the differences in accordance with Student's t and variance analysis.

The results of the tests carried out on the patients from the first group are set forth in Table 1.

stressed that, despite the different ages of the two groups of individuals examined, the difference between the mean values±D.S. at the time $t_0$ of the two groups is *not* statistically significant ($t = 1.347225933$; degrees of freedom: 10), thereby the two groups should be regarded as being statistically homogeneous.

Statistical analysis of the mean values±D.S. at the thirtieth minute brings out a statistically significant difference ($P < 0.002$) in favor of the group treated with "SORGENTE PANNA" oligomineral water ($T = 5.318190528$; degrees of freedom: 10).

Likewise, at the sixtieth minute, the difference between the mean values obtained with demineralized water of Example 2 and "SORGENTE PANNA" oligomineral water liposomes of Example 1 has shown

TABLE 1

Determination of the moisturizing gradient of the stratum corneum by corneometry of the: forehead, right temporal and cheekbone region, left temporal and cheekbone region, right and left cheeks, chin, and mean of the values across the whole face under basal conditions and after 30, 60 minutes from liposomic application in demineralized water plus collagen.

| T   | F           | T.C.dx      | T.C.sin     | C.dx        | C.sin       | Chin        | Overall Corneometry |
|-----|-------------|-------------|-------------|-------------|-------------|-------------|---------------------|
| 0   | 72.2 ± 28.3 | 83.0 ± 16.5 | 98.7 ± 2.5  | 90.2 ± 6.7  | 97.2 ± 7.6  | 96.2 ± 6.9  | 89.5 ± 10.3         |
| 30' | 77.2 ± 12.4 | 91.7 ± 5.3  | 91.2 ± 9.4  | 83.5 ± 8.1  | 88.2 ± 5.6  | 78.5 ± 19.8 | 85.05 ± 6.3         |
| 60' | 69.2 ± 23.9 | 84.7 ± 9.0  | 89.5 ± 16   | 79.5 ± 7.7  | 81.5 ± 8.8  | 81.7 ± 8.5  | 81.01 ± 6.7         |

T = time;
F = Forehead;
T.C.dx = Right temporal and cheekbone region;
T.C.sin = Left temporal and cheekbone region;
C.dx = Right cheek;
C.sin = Left cheek;
Overall Corneometry = Mean of the corneometric values in the various skin regions of the face.

The results of the test carried out on the patients in the second group, as treated with "SORGENTE PANNA" oligomineral water liposomes plus GAG precursors, are set forth in the following Table 2.

to have statistical significance ($P < 0.02$; $t = 2.36832777$; degrees of freedom: 10).

I claim:

1. A product for moisturizing a human's skin, which

TABLE 2

Determination of the moisturizing gradient of the stratum corneum by corneometry of the: forehead, right temporal and cheekbone region, left temporal and cheekbone region, right and left cheeks, chin, and mean of the value across the whole face under basal conditions and after 30, 60 minutes from application of "SORGENTE PANNA" oligomineral water liposomes plus GAG.

| T   | F            | T.C.dx        | T.C.sin       | C.dx          | C.sin         | Chin          | Overall Corneometry |
|-----|--------------|---------------|---------------|---------------|---------------|---------------|---------------------|
| 0   | 93.3 ± 9.71  | 95.3 ± 10.99  | 94.8 ± 12.00  | 93.9 ± 13.42  | 94.5 ± 14.16  | 100.9 ± 6.78  | 95.4 ± 2.8          |
| 30' | 101.9 ± 9.18 | 100.7 ± 11.29 | 99.7 ± 11.23  | 99.4 ± 13.59  | 99.6 ± 10.51  | 108.6 ± 4.69  | 101.6 ± 3.5         |
| 60' | 100.5 ± 9.64 | 96.9 ± 10.39  | 98.7 ± 9.76   | 98.8 ± 8.84   | 98.3 ± 11.84  | 108.4 ± 6.73  | 100.2 ± 4.1         |

The data set forth in the Tables are summarized graphically by the histograms shown in FIGS. 1 to 7, and 1A to 7A, respectively.

A review of the data set forth in the Tables and in the drawing figures reveals that, whereas the preparation of Example 2 proved ineffective at the sixtieth minute to improve the mean values of skin moisturization, except for a modest increase at the thirtieth minute, in all of the face regions observed, the preparation according to the present invention has shown a moisturizing effect which was already evident at the thirtieth minute and was retained in most instances up to the sixtieth minute, that is throughout the test period.

Figure 7A:
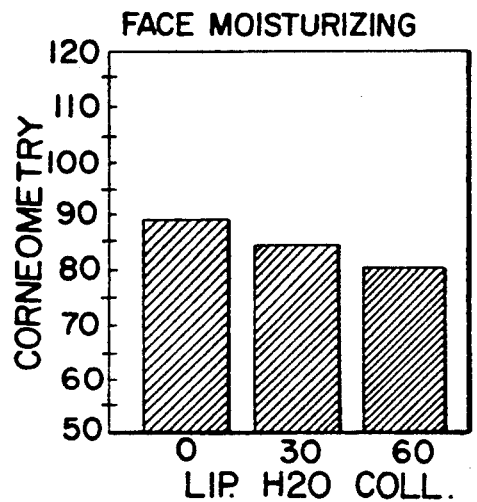

The pattern of the mean overall values related to the sum of the corneometric values in all the skin regions of the face examined, clearly shows that the preparation of liposomes in demineralized water and collagen has been *unable* to alter to a statistically significant extent the corneometric values (cfr. FIG. 7A) in the case study carried out.

Figure 7B:
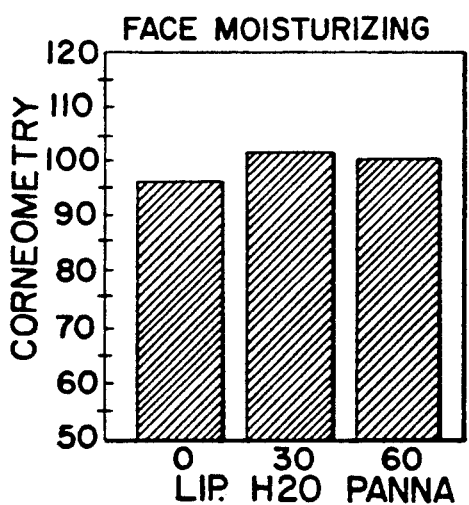

By contrast, the treatment with "SORGENTE PANNA" oligomineral water liposomes yielded the overall mean values set forth in FIG. 7B. It should be product comprises:
liposomes which enclose mineral water, and which have associated therewith immediate biochemical precursors of asulfurate glucosaminoglycanes.

2. The product according to claim 1, wherein the mineral water is an oligomineral water.

3. The product according to claim 2, wherein said liposomes enclose SORGENTE PANNA oligomineral water.

4. A moisturizing composition for a human's skin, the composition comprising complex liposomes which enclose a mineral water, and which have associated therewith an immediate biochemical precursor of an asulfurate glucosaminoglycan;

the moisturizing composition being prepared by a process comprising the step of:
forming a microdispersion of a phospholipid and an immediate biochemical precursor of an asulfurate glycosaminoglycan, in a solution which comprises the mineral water.

5. The moisturizing composition according to claim 4, wherein the mineral water is an oligomineral water.

6. The moisturizing composition according to claim 4, wherein the mineral water is SORGENTE PANNA oligomineral water.

7. A method for moisturizing a human's skin, which method comprises:
applying topically to the skin a composition comprising liposomes which enclose mineral water, and which have associated therewith immediate biochemical precursors of asulfurate glucosaminoglycanes.

8. The method according to claim 7, wherein said mineral water is an oligomineral water.

9. The method according to claim 8, wherein said oligomineral water is SORGENTE PANNA oligomineral water.

10. The method according to claim 7, wherein the mineral water liposome composition is dispensed in a nebulized or atomized state from small bottles charged with a suitable propellant.

11. A method for moisturizing a human's skin, which method comprises
applying topically to the skin a moisturizing composition comprising complex liposomes which enclose a mineral water, and which have associated therewith an immediate biochemical precursor of an asulfurate glucosaminoglycan;
the moisturizing composition being prepared by a process comprising the step of:
forming a microdispersion of a phospholipid and an immediate biochemical precursor of an asulfurate glycosaminoglycan, in a solution which comprises the mineral water.

12. The method of claim 11, wherein the mineral water is an oligomineral water.

13. The method of claim 11, wherein the mineral water is SORGENTE PANNA oligomineral water.

* * * * *